United States Patent
Zhang et al.

(10) Patent No.: US 11,698,354 B1
(45) Date of Patent: Jul. 11, 2023

(54) PORTABLE XRF DATA SCREENING METHOD FOR HEAVY METAL CONTAMINATED SOIL

(71) Applicant: BEIJING MUNICIPAL RESEARCH INSTITUTE OF ENVIRONMENTAL PROTECTION, Beijing (CN)

(72) Inventors: Lina Zhang, Beijing (CN); Lin Jiang, Beijing (CN); Tianxiang Xia, Beijing (CN); Xiaoying Zhu, Beijing (CN)

(73) Assignee: BEIJING MUNICIPAL RESEARCH INSTITUTE OF ENVIRONMENTAL PROTECTION, Beijing (CN)

( * ) Notice: Subject to any disclaimer, the term of this patent is extended or adjusted under 35 U.S.C. 154(b) by 0 days.

(21) Appl. No.: 18/069,895

(22) Filed: Dec. 21, 2022

(30) Foreign Application Priority Data

Dec. 29, 2021 (CN) .......................... 202111636480.7

(51) Int. Cl.
*G01N 23/223* (2006.01)
*G01N 23/2206* (2018.01)
*G01N 23/2202* (2018.01)

(52) U.S. Cl.
CPC ....... *G01N 23/223* (2013.01); *G01N 23/2202* (2013.01); *G01N 2223/076* (2013.01); *G01N 2223/1016* (2013.01); *G01N 2223/301* (2013.01); *G01N 2223/304* (2013.01); *G01N 2223/3037* (2013.01); *G01N 2223/616* (2013.01); *G01N 2223/645* (2013.01); *G01N 2223/652* (2013.01)

(58) Field of Classification Search
None
See application file for complete search history.

(56) References Cited

U.S. PATENT DOCUMENTS 4,848,590 A  7/1989  Kelly

FOREIGN PATENT DOCUMENTS

| CN | 101520421 A |   | 9/2009 |   |   |
|---|---|---|---|---|---|
| CN | 202683502 U |   | 1/2013 |   |   |
| CN | 103743769 A |   | 4/2014 |   |   |
| CN | 106706691 A | * | 5/2017 | .......... | G01N 23/223 |
| CN | 106706691 A |   | 5/2017 |   |   |

(Continued)

OTHER PUBLICATIONS

Suh et al "A Rapid, Accurate, and Efficient Method to Map Heavy Metal-Contaminated Soils of Abandoned Mine Sites Using Converted Portable XRF Data and GIS." International Journal of Environmental Research and Public Health (2016) 13, 1191 (Year: 2016).*

(Continued)

*Primary Examiner* — Thomas R Artman

(57) ABSTRACT

Provided is a portable XRF data screening method for heavy metal contaminated soil, relating to the technical field of heavy metal contamination test. The method includes the following steps: (1) laboratory test; (2) XRF test; and (3) calculation of a recheck interval: dividing test data into four areas by a contaminant screening value $X_c$ as a horizontal line and a correlation-derived site screening value as a vertical line to calculate the recheck interval. The method is simple and efficient, and is beneficial to saving investigation costs and shortening a project cycle.

9 Claims, 8 Drawing Sheets

(56) References Cited

FOREIGN PATENT DOCUMENTS

| CN | 108535301 A | 9/2018 |
| CN | 111610207 A | 9/2020 |

OTHER PUBLICATIONS

Kim et al "Assessing Statistically Significant Heavy-Metal Concentrations in Abandoned Mine Areas via Hot Spot Analysis of Portable XRF Data." International Journal of Environmental Research and Public Health (2017) 14, 654 (Year: 2017).*

Liu Chang et al., "Comparative Study of ICP-MS and XRF for Determination of Heavy Metals Content in PM_(2.5)", Environmental Science & Technology, Apr. 15, 2018, pp. 66-70.

Mei Yanjun et al., "Measurement o f S r/C a Ratio in Tridacna spp. Shells from South China Sea: A Comparison of SR-XRF and ICP-OES Analysis Methods", Spectroscopy and Spectral Analysis, vol. 38, No. 5, May 15, 2018, pp. 1640-1647.

* cited by examiner

PORTABLE XRF DATA SCREENING METHOD FOR HEAVY METAL CONTAMINATED SOIL

CROSS REFERENCE TO RELATED APPLICATIONS

This application claims foreign priority of Chinese Patent Application No. 202111636480.7, filed on Dec. 29, 2021 in the China National Intellectual Property Administration, the disclosures of all of which are hereby incorporated by reference.

TECHNICAL FIELD

The present invention relates to the technical field of heavy metal contamination test, in particular to a portable XRF data screening method for heavy metal contaminated soil.

BACKGROUND

At present, the overall situation of soil environments is not optimistic. In some areas, soil contamination is serious, and the type of contamination is mainly inorganic, which easily causes heavy losses. Regular monitoring of heavy metal contaminated areas and pilot demonstration of contamination control and remediation are important tasks for environmental protection and comprehensive treatment of soil in the near future.

The test and analysis of heavy metals are the basis of contamination investigation and treatment. At present, there are many test methods for heavy metals. Uncertainty is often attributed to sample treatment and test methods in early site investigation, data quality is equated to data accuracy, and accordingly, a series of strict analysis procedures and certification conditions are established to assess test technologies. Traditional determinations of total heavy metals in soil generally adopt a digestion-dilution-determination mode, which can effectively analyze heavy metal ions in samples with relatively high sensitivity, but most of such determinations require large instruments, high-cost analysis methods and long sample analysis cycles, and the site investigation requires a lot of reliable data, where the accuracy and quantity of data directly affect the investigation results and remediation decisions. Generally, traditional laboratory tests are close to the true values of samples, but the number of samples is often sacrificed due to budget, so there are probably contaminated areas that cannot be monitored, which makes the remediation decisions greatly uncertain, resulting in the problems of uncertainty in the depiction of contamination distribution and the like. In order to solve the problems in traditional site investigation, the United States has tried and established a Triad mode of contaminated sites, in which real-time measurement technology is its main component, including not only on-site instantaneous measurement but also technologies that the measurement period does not affect on-site decision-making, such as kits, portable instruments, in-situ probes, mobile laboratories, and laboratory tests that can provide results quickly, which can meet the needs of a large amount of data, reduce the uncertainty in the process of site investigation and remediation, greatly shorten a project cycle, improve the efficiency of site investigation and remediation, and reduce project costs.

In response to heavy metal contaminant tests, the portable X-ray fluorescence spectroscopy (XRF) has been applied in many fields as a relatively mature test method and widely recognized for its advantages of simple pretreatment, low test cost, fast analysis speed, high test accuracy, wide range of test elements, strong applicability, good stability, etc. Van Cott et al. compared the relative errors of X-ray fluorescence spectrometry and atomic absorption spectrometry in elemental analysis of standard samples, and the results showed that the relative deviations of the two were not significant. Lake Success Business Park, a lead contaminated site in the United States, analyzed the correlations between on-site XRF, Bagged-sample XRF, In-situ XRF and experimental test methods 3050/6010, evaluated the accuracy of various test methods, thought that the XRF test method was accurate, sensitive and accurate enough and its data could support remediation decision-making, and found that the correlation between XRF and laboratory was better when the preparation of samples was more rigorous and close to laboratory analysis. Min Jang et al. used XRF to detect Zn, As, etc. and analyzed the correlation with laboratory methods, showing that XRF could effectively determine hot spots. Bernick, M. B et al. introduced an XRF test method and its statistical analysis method with laboratory test results in detail, and thought that the correlation coefficient between XRF and laboratory test results was higher than 0.7, which could assist decision-making.

In fact, the truth values of respondents are unknown, and the data results of any test method are true estimates, so only high-precision and expensive laboratory analysis or simple and rapid test methods hardly meet the needs of decision-making. Studies found, for heavy metals in soil, under the condition of good correlation between XRF test results and traditional laboratory test results, most XRF test results can assist decision-making, that is, the laboratory concentrations of samples that pass XRF test also reach the standard, and the laboratory concentrations of samples that fail in XRF test also do not reach the standard. However, due to the test errors, a small number of XRF test results and laboratory results easily lead to misjudgment (false positive or false negative) or uncertainty of judgment. Some studies in the United States came to recognize this uncertainty, and used a safety factor to reduce the error rate of determination, for example, used laboratory test to verify the points where the test values were near ±20% of a screening value. Bernick, M. B et al. thought that at least 10% of the total sample size needed to be verified by a laboratory method. That is, the scope of a recheck interval is determined subjectively, and there is no study to determine an objective and reasonable recheck interval according to its error.

In view of the problems existing in the prior art, it is very necessary to find a simple, efficient and low-cost data screening method for heavy metal contaminated soil.

SUMMARY

Aiming at the problems existing in the prior art, the present invention provides a portable XRF data screening method for heavy metal contaminated soil, which is simple and efficient, and is beneficial to saving investigation costs and shortening a project cycle.

To achieve the above objective, the technical solution adopted by the present invention is as follows:

The present invention provides a portable XRF data screening method for heavy metal contaminated soil, including the following steps:

(1) Laboratory test: testing a soil sample in a laboratory to obtain a laboratory test value, which is identified as a true value and denoted by LAB;

(2) XRF test: calibrating an X-ray fluorescence spectrometer with a calibrating sample, and testing pretreated soil with the calibrated X-ray fluorescence spectrometer to obtain an X-ray fluorescence spectrometer test value, which is identified as an estimated value and denoted by XRF; and (3) Calculation of a recheck interval: dividing test data into four areas by a contaminant screening value $X_c$ as a horizontal line and a correlation-derived site screening value as a vertical line;

calculating a recheck interval with a number of samples n, a standard value μ and a sample standard deviation S, specifically including:

① determining a significant level α;

② calculating the sample standard deviation S;

③ determining a critical value $C=t_\alpha(n-1)$ according to the degree of freedom df=n−1 and α; and ④ calculating a lower recheck interval limit $\mu-C\times S/\sqrt{n}$, and an upper recheck interval limit $\mu+C\times S/\sqrt{n}$, thus obtaining a recheck interval $[\mu-C\times S/\sqrt{n}, \mu+C\times S/\sqrt{n}]$; and determining, according to the situation that the sample falls into the four areas in the recheck interval, whether or not to further recheck the sample.

Further, the significant level in step ① is 0.05 and/or 0.01.

Further, the pretreatment in step (2) specifically includes: air-drying, grinding, sieving and drying the soil sample.

Further, the four areas in step (3) are respectively area I, area II, area AA and area BB.

Further, the area I is a class I error decision failure area, the area II is a class II error decision failure area, the area AA is an area where both laboratory test and XRF test exceed the standard, and the area BB is an area where both laboratory test and XRF test do not exceed the standard.

Further, the critical value C in step (3) is obtained from a distribution critical value table.

Further, before the recheck interval is calculated in step (3), the method further includes checking the distribution patterns of XRF and XRF' test data of each contaminant in the site: deriving real-time tested XRF'=(LAB−b)/a according to a correlation formula between the true value and the estimated value: LAB=a×XRF+b; normalizing the values of XRF' and XRF according to a percentage as a pair of parallel samples for statistical test, and if the values obey a normal distribution, performing the next step of calculating a recheck interval, otherwise, if the values do not obey a normal distribution, eliminating relevant test data.

Further, determining, according to the situation that the sample falls into the four areas in the recheck interval, whether or not to further recheck the sample in step (3) is specifically: when the sample falls into the area I or the area II in the recheck interval, rechecking the sample, otherwise, skipping rechecking the sample.

Further, the method of the present invention can be applied to the screening of heavy metal contaminated soil.

The technical effects obtained by the present invention are as follows:

In the present invention, soil samples are tested by using an XRF method and verified by contrastive analysis with laboratory data, and the samples that need to be rechecked are screened, so this method is simple and efficient and is beneficial to saving investigation costs and shortening a project cycle.

BRIEF DESCRIPTION OF FIGURES

FIG. 3A, FIG. 3B, FIG. 3C, and FIG. 3D are correlation analysis diagrams of XRF and LAB data of heavy metals Cr, As, Zn and Pb, respectively;

FIG. 4A, FIG. 4B, FIG. 4C, and FIG. 4D are probability diagrams of Cr, As, Zn and Pb (normal-95% confidence interval), respectively; FIG. 5B, FIG. 5C, and FIG. 5D are schematic diagrams of recheck intervals of Cr, As, Zn and Pb, respectively.

DETAILED DESCRIPTION

Figure 1:
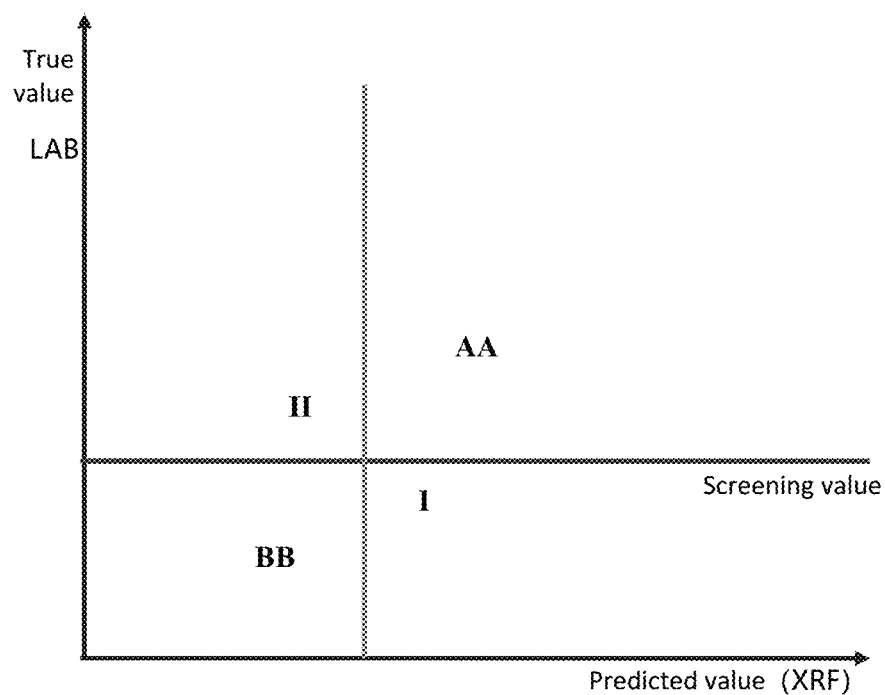
FIG. 1 is a schematic diagram of division of test data areas.

The embodiments of the present invention will be described below through specific examples. Those skilled in the art could easily understand other advantages and effects of the present invention from the content disclosed in this specification. The present invention can also be implemented or applied through other different specific embodiments. The details in this specification can also be based on different viewpoints and applications, and various modifications or changes can be made without departing from the spirit of the present invention.

Before the specific embodiments of the present invention are further described, it should be understood that the protection scope of the present invention is not limited to the following specific implementation schemes. It should also be understood that the terms used in the examples of the present invention are used to describe the specific implementation schemes, and are not to limit the protection scope of the present invention.

When the embodiments present numerical ranges, it should be understood that two endpoints of each numerical range and any value between the two endpoints could be used, unless otherwise stated in the present invention. Unless otherwise defined, all technical and scientific terms used herein have the same meaning as those generally understood by persons of ordinary skill in the art to which the present invention pertains.

Example 1

1. Overview of Site

The site in this case is a chemical plant near the East Fourth Ring Road in Beijing, covering an area of 339,000 m². Before 1950, the site was mainly a farmland and wasteland, and had never engaged in industrial production activities. From 1950 to the end of 1980s, an organic chemical plant in Beijing was built at this site, and mainly produced arsenic salts and chromium salts. The production process was very backward at that time. According to the historical data of the plant, before 1973, various wastes produced in the plant were directly discharged into the surrounding environment without any treatment, and the discharge amount of $Cr^{6+}$ at a discharge port of its reagent branch plant was 42 kg·$a^{-1}$. The chemical plant stopped production around 2004 and was gradually moved, and the site was developed into a residential and commercial land. According to the analysis on the historical production data, it can be seen that the soil in the plant area was very likely to be contaminated by heavy metals such as As and Cr, so the soil in the plant area must be sampled and analyzed to further determine whether the soil in the plant area was really contaminated by the heavy metals.

2. Sample Collection and Test

Sample collection: according to the grid distribution of a system (300 m*300 m), the contaminated site was sampled in May 2014, and 39 samples of surface soil (0-20 cm) were collected for laboratory test and portable X-ray fluorescence spectrometer test respectively.

Traditional laboratory test (ICP): after heavy metals Cr, Pb and Zn in soil were digested by HF-HCLO4-HNO3 and As was digested by HNO3-HCL, the heavy metals were determined by inductively coupled plasma-atomic emission spectrometry (ICP-AES/EPA6010C), national standard soil samples were added during the whole course for quality control, and basic physical and chemical properties were analyzed according to conventional methods.

XRF laboratory test (XRF): a portable X-ray fluorescence spectrometer (XRF) may be operated in situ or in a laboratory. Studies showed that when the preparation of samples was more rigorous and close to traditional laboratory analysis preparation methods, the correlation between XRF test results and traditional laboratory analysis results was better. A laboratory determination method was used in this study: the soil samples were air-dried, ground, screened with a 200-mesh sieve, and dried at 105° C. for 2 h, and the pretreated soil samples were put into specific sample cups for measurement, where the measuring instrument was NOTON XLp 300 portable X-ray fluorescence spectrometer (XRF) of Thermo Fisher Company, U.S.A, the measuring time was 90 s, and the measurement was repeated three times. Before use, the XRF instrument was calibrated with its calibrating sample, and meanwhile, the main parameters of the instrument were tested, debugged and selected with soil labelling samples, such that the condition of the instrument itself reached the best to eliminate or reduce interference between elements and improve the stability of test.

3. Data Evaluation Method

In this study, a recheck interval was calculated by analyzing the errors between laboratory test results (ICP) and portable instrument results (XRF). First, the correlation between real-time test results and laboratory analysis results was analyzed. If laboratory test values are defaulted as true values, XRF test data were considered as estimated values and XC represented screening values of contaminants, the test results were divided into four areas based on laboratory screening values and correlation-derived on-site screening values, where areas I and II represented class I error (false positive) and class II error (false negative) decision failure areas respectively, I represented that the real-time test data exceeded the standard but the laboratory data did not exceed the standard, the class II errors represented that the real-time test data did not exceed the standard but the laboratory data exceeded the standard, and areas AA and BB represented decision areas where the data results were consistent with the true values, i.e., the real-time test data and the laboratory analysis data exceeded the standard or not at the same time.

Figure 2:
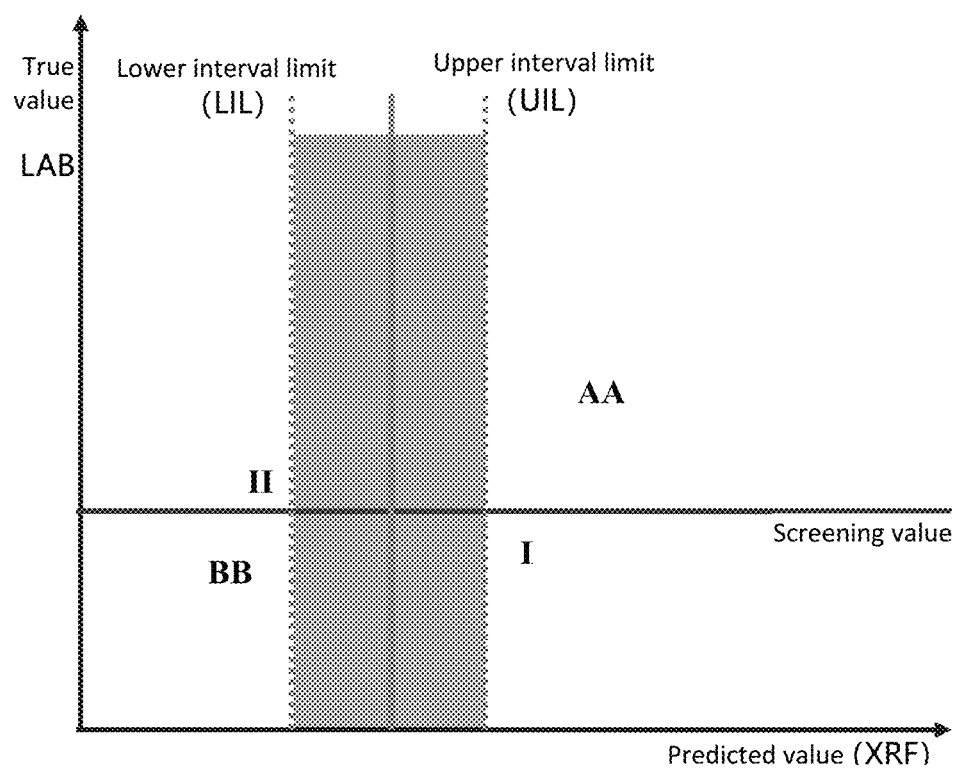
FIG. 2 is a schematic diagram of division of an on-site quick screening recheck interval.
Figure 3A:
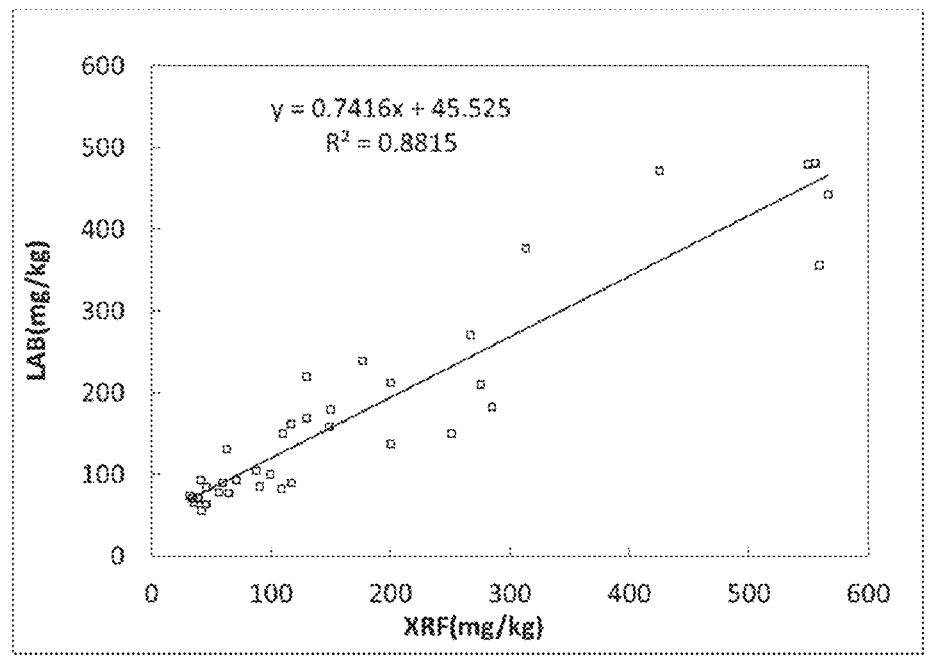
FIGS. 3A-3D show correlation analysis diagrams of on-site XRF and LAB data, where
Figure 3B:
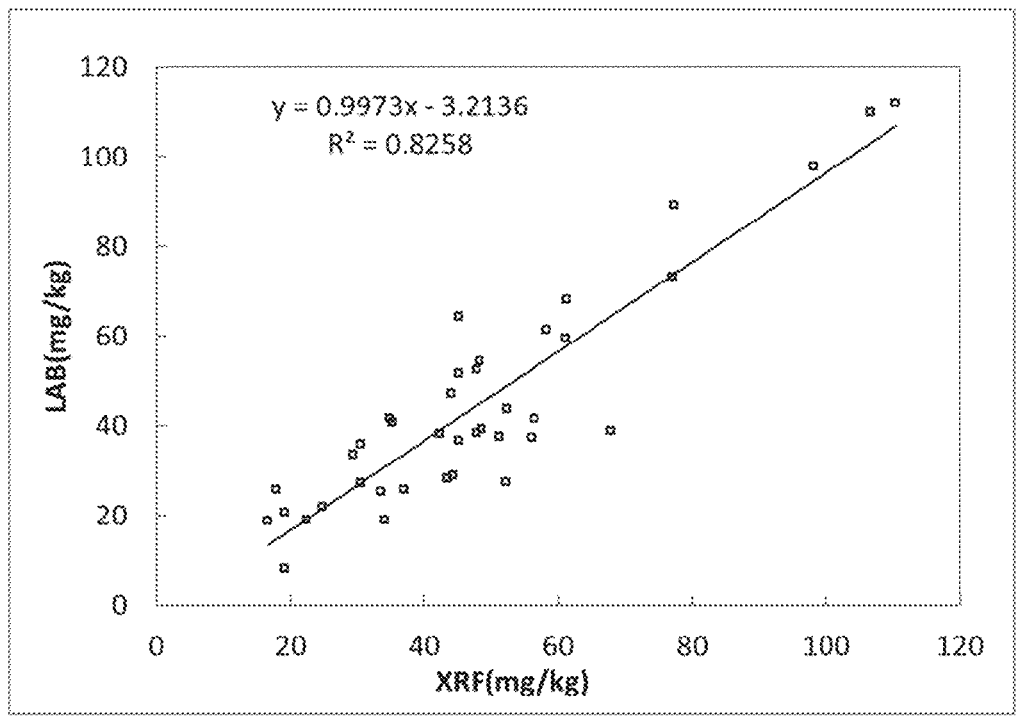
Figure 3C:
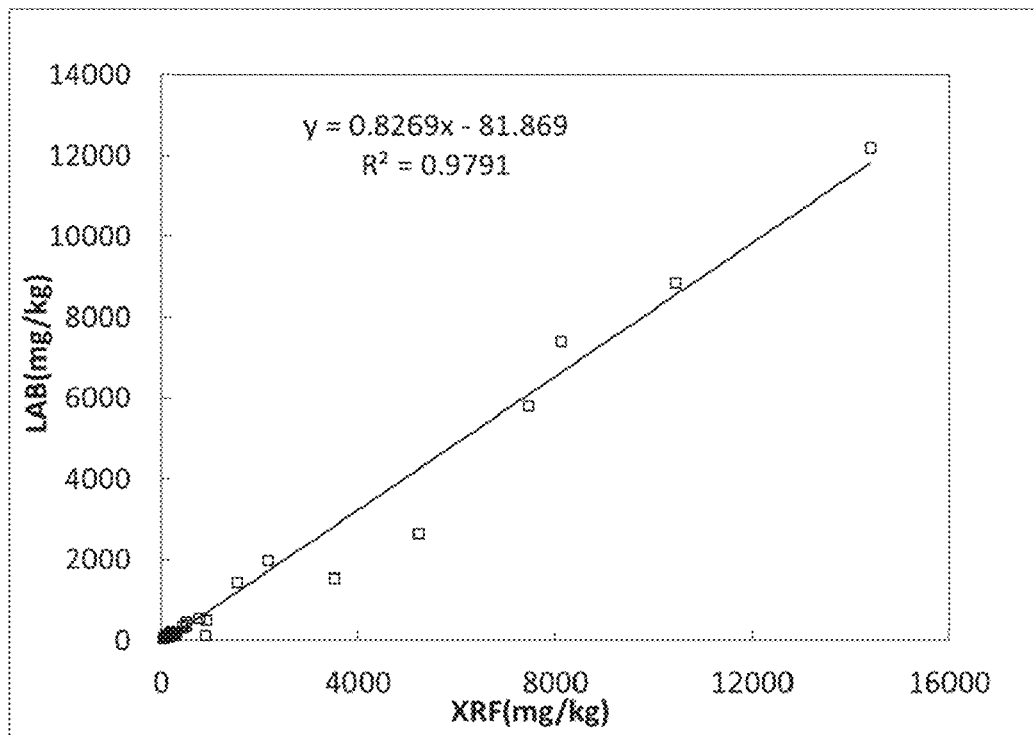
Figure 3D:
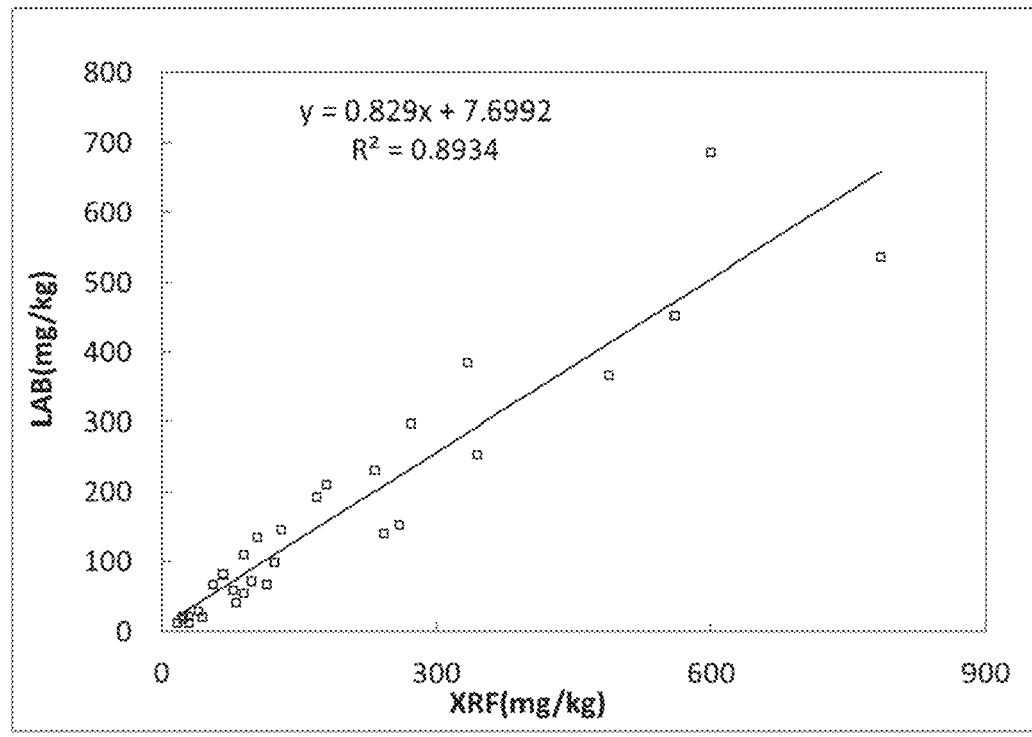
Figure 4A:
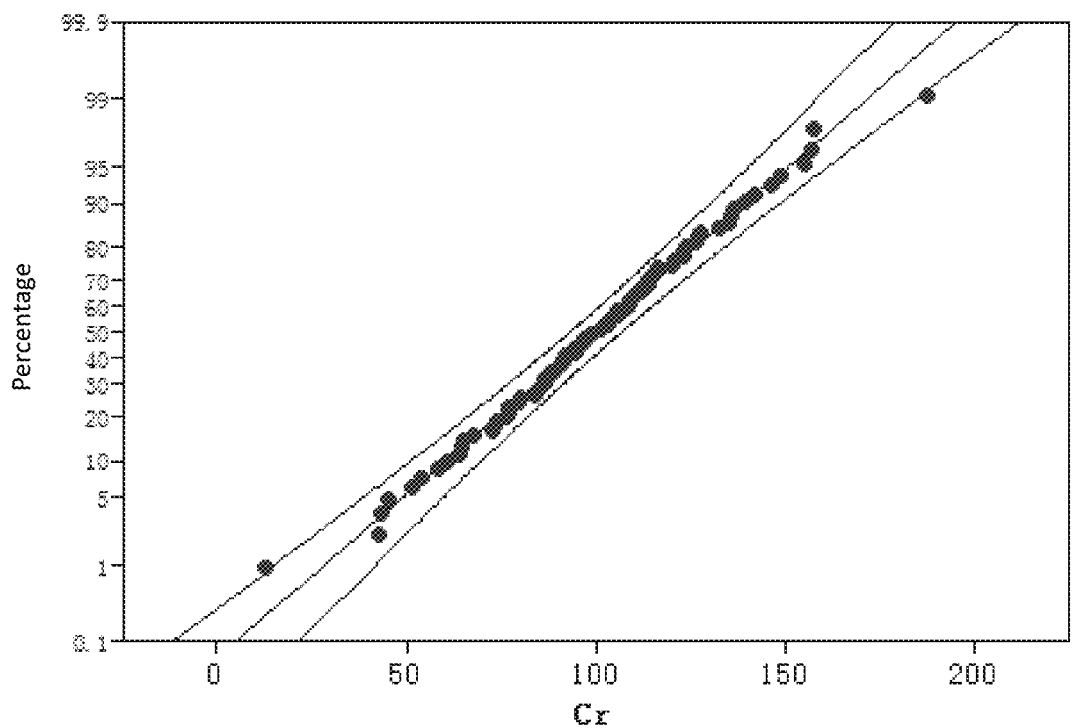
FIGS. 4A-4D show test diagrams of XRF and XRF' data distribution of heavy metals, where
Figure 4B:
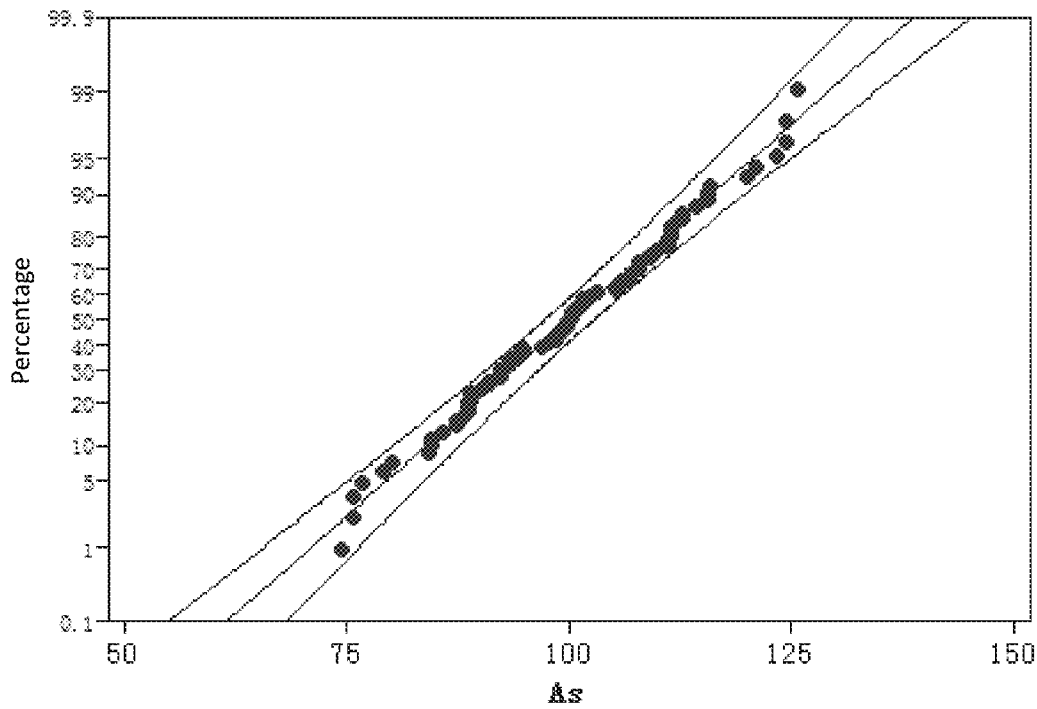
Figure 4C:
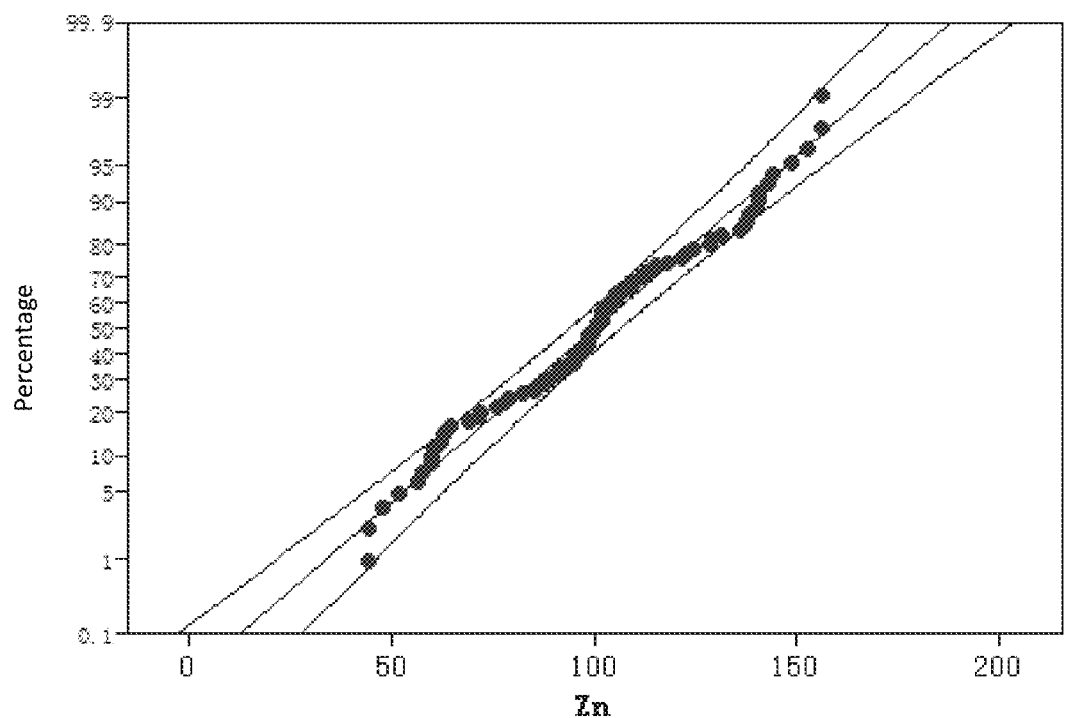
Figure 4D:
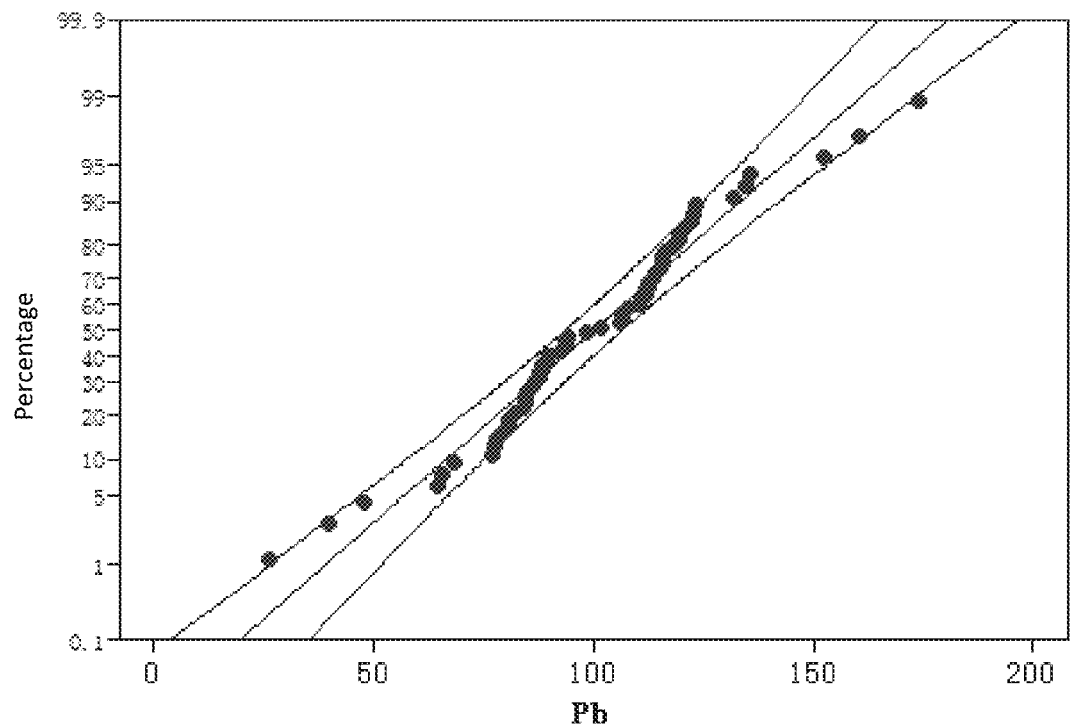
Figure 5A:
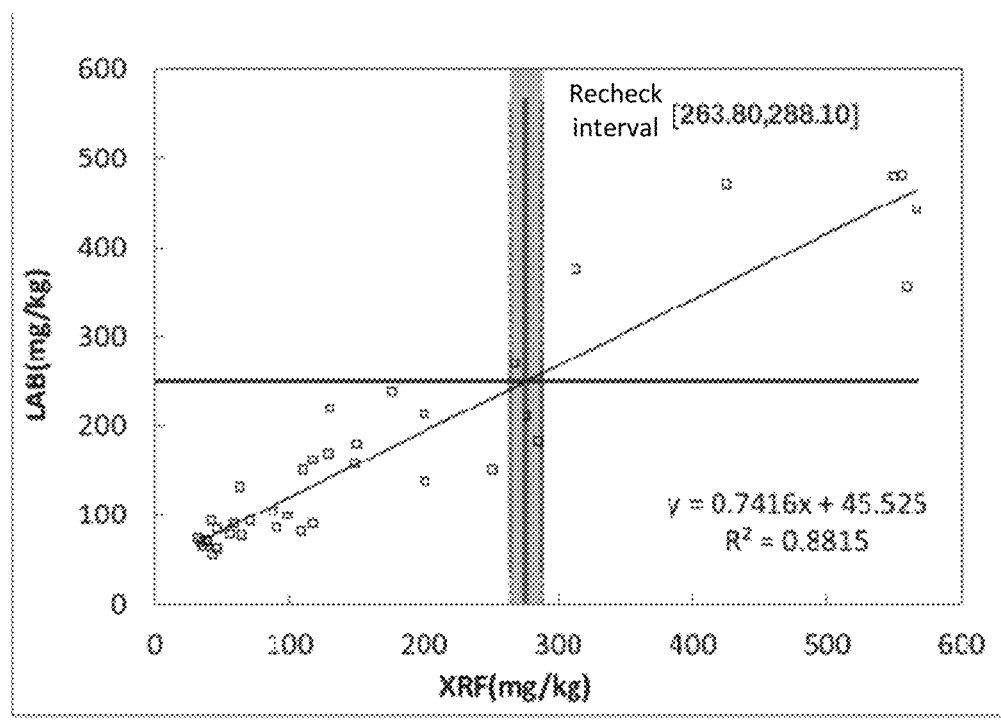
FIGS. 5A-5D show schematic diagrams of XRF recheck intervals of heavy metals, where 5A.
Figure 5B:
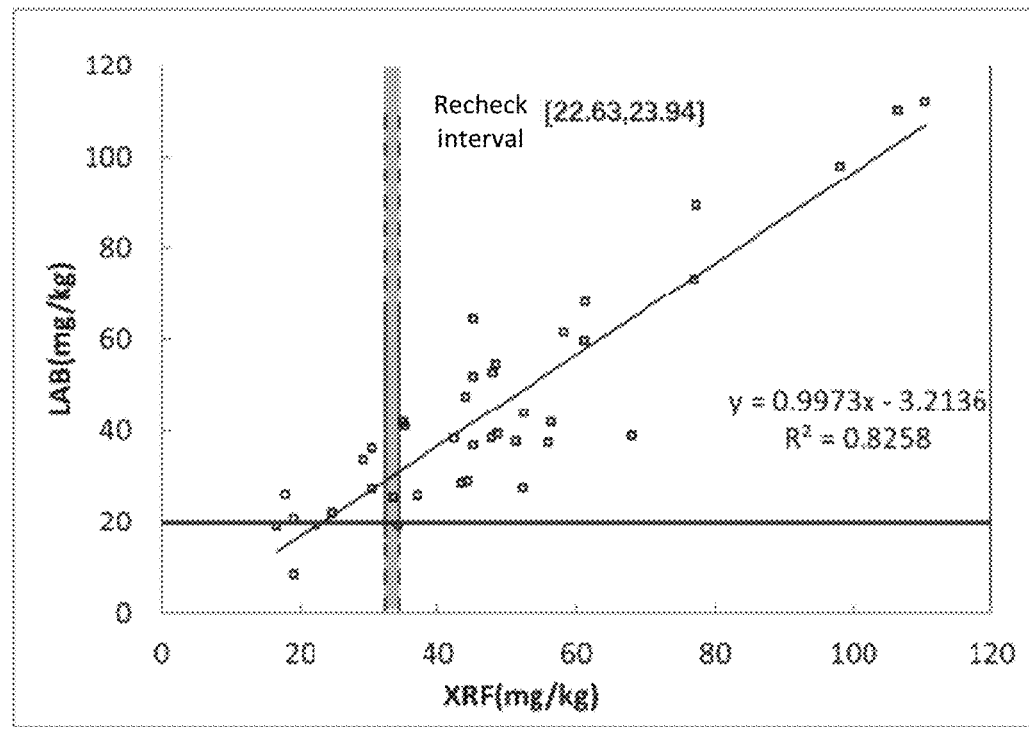
Figure 5C:
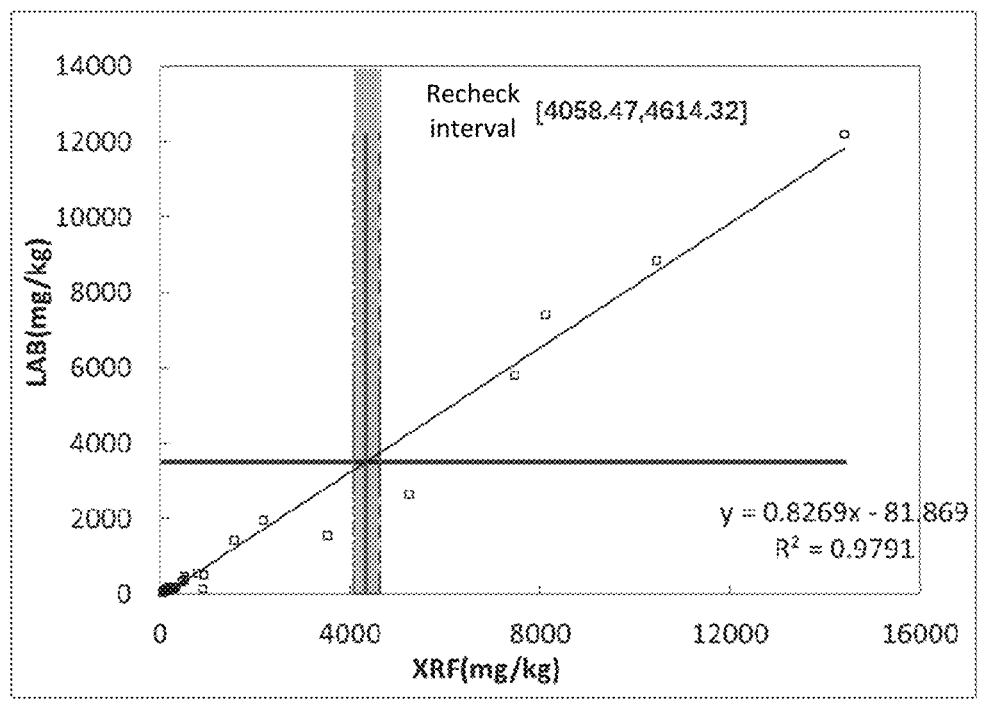
Figure 5D:
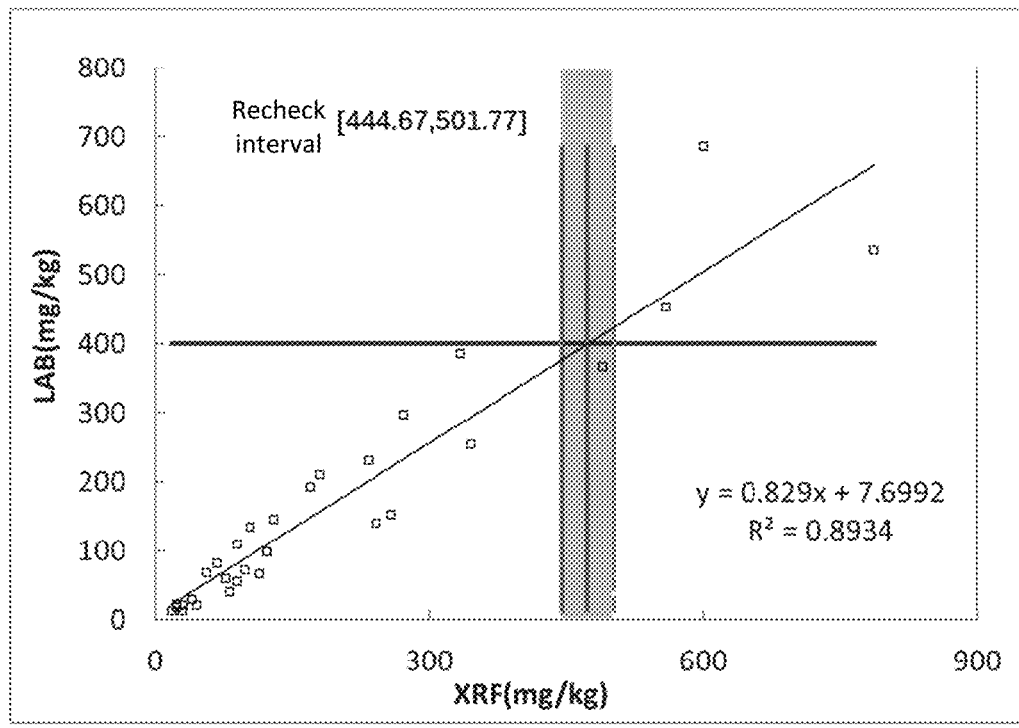

Because of the characteristics of real-time test, its errors easily produced areas of unclear conclusions and easily caused uncertainty or failure in determination, so further laboratory analysis was required for verification. The purpose of verification was to reduce the uncertainty of analysis, obtain an interval that needed laboratory test for recheck, and effectively combine the laboratory accuracy with the quantity of rapid test to make correct decisions as much as possible. The existence of the recheck interval can reduce the class I error and class II error areas, as shown in FIG. 1 and FIG. 2, where the dark shadow area in FIG. 2 represented a recheck area, areas AA and BB represented areas where the laboratory and on-site test results were consistent, and areas I and II represented two types of error areas respectively.

It was assumed that the laboratory test values were true values. According to the correlation formula LAB=a× XRF+b between the laboratory test and XRF test values (denoted by LAB and XRF respectively), possible true values of real-time test may be derived as XRF'=(LAB−b)/a. The values of XRF' and XRF were normalized according to a percentage as a pair of parallel samples for statistical test, and the obtained interval without significant differences was the recheck interval.

For example, the number of samples tested was n, the standard value (i.e., ICP standard value) was μ, and the standard deviation of samples was S. The steps for calculating a recheck interval were as follows: ① a significant level α was determined, usually α=0.05 or α=0.01; the significant level only indicated the reliability of conclusions, that is, the reliability of negating invalid hypothesis at the level of 0.01 was 99%, while the reliability of negating invalid hypothesis at the level of 0.05 was 95%; ② the standard deviation of samples S was calculated; ③ a critical value $C=t_\alpha(n-1)$ was determined according to the degree of freedom df=n−1 and a (look up a t distribution critical value table in a statistical manual), for example, n=8, α=0.05, t=2.365; and ④ a lower limit $\mu-C\cdot S/\sqrt{n}$, and upper limit $\mu+C\cdot S/\sqrt{n}$, of the recheck interval were calculated to obtain the recheck interval $[\mu-C\times S/\sqrt{n}, \mu+C\times S/\sqrt{n}]$.

4. Results and Discussions (1) ICP and XRF Test Results and Correlation Analysis In this study, the standard values of the residential land in the screening values of soil environmental risk assessment of Beijing site (DB 11/T 811-2011) were used as screening standards of the site investigation. Samples whose concentrations were lower than the screening values were used as blank samples, and the determination was repeated for 7 times. The XRF test limits of various heavy metals at this site were calculated by taking 3 times of standard deviations, and the results were all lower than the background values and screening values of elements in this area, indicating that XRF can be used for rapid test of heavy metal contamination in soil of this site.

According to the XRF results, the concentration of As was about 87.18% and exceeded the screening value by 20 mg/kg, the over-standard rates of Cr, Zn and Pb were 20.51%, 12.82% and 12.90% respectively, and the over-standard rates tested by the two methods were relatively close. The data of the four elements tested by XRF were lower than the ICP test data. The average values of Cr, As and Pb tested by the two methods were a little different, while the average values of Zn tested by the two methods were greatly different.

TABLE 1

Descriptive statistics of heavy metal content in soil

| Heavy metal | Sample size tested | Test method | Maximum value | Minimum value | Average value | Standard deviation (SD) | Over-standard quantity | Screening criteria |
|---|---|---|---|---|---|---|---|---|
| Cr | 39 | LAB | 566.31 | 31.82 | 169.95 | 161.44 | 7 | 250 |
|  |  | XRF | 481.00 | 56.00 | 173.01 | 130.37 | 8 |  |
| As | 39 | LAB | 110.46 | 16.62 | 48.02 | 22.52 | 35 | 20 |
|  |  | XRF | 112 | 8.4 | 44.68 | 24.71 | 34 |  |
| Zn | 39 | LAB | 14408.17 | 50.03 | 1557.20 | 3221.63 | 4 | 3500 |
|  |  | XRF | 12200.00 | 51.8 | 916.39 | 2692.08 | 5 |  |
| Pb | 31 | LAB | 786.00 | 17.83 | 188.15 | 191.73 | 3 | 400 |
|  |  | XRF | 686.00 | 12.60 | 163.68 | 168.16 | 4 |  |

Correlation analysis was carried out on the measured values of Cr, As, Zn and Pb in soil obtained by traditional laboratory preservation, treatment and testing for heavy metal samples and the data tested by a portable X-ray spectrometer. As shown in FIGS. 3A-3D, the results showed that there was a good correlation between the two test results of four contaminants of concern in this site ($R^2 > 0.7$).

(2) Calculation and Obtaining of Recheck Interval

First, the distribution patterns of XRF and XRF' test data of contaminants in the site were tested, and the results were shown in FIGS. 4A-4D. It can be seen from FIGS. 4A-4D that the normalized w(Cr), w(As), w(Pb), and w(Zn) all obeyed normal distribution. For the contaminant test data obeying the normal distribution, an investigation space was calculated by statistical test.

nated area; two points fell into the class II error area, accounting for 5.13% of the total number of samples, for example, the XRF test value was 17.81 mg/kg, while the ICP test value was 25.9 mg/kg, i.e., the actual value exceeded the standard but the XRF test value did not exceed the standard, such that the contaminated area was neglected; the recheck interval of As was [22.63, 23.94], which needed to be verified by ICP test; and no sample test value in this batch fell in the recheck interval.

For Zn in the soil of the site, 37 of the 38 samples were determined as consistent, accounting for 97.36% of the total number of samples, including 4 samples determined to exceed the standard and 34 samples determined not to exceed the standard; and one sample fell in the class I area, accounting for 2.56% of the total number of samples. The

TABLE 2

Statistical test results and recheck interval analysis

| Contaminant | n | Standard deviation | Critical value C | $C \cdot S/\sqrt{n}$ | ICP standard value | XRF' standard value | Lower limit of recheck interval | Upper limit of recheck interval |
|---|---|---|---|---|---|---|---|---|
| Cr | 78 | 19.53 | 1.991 | 4.4 | 250 | 275.95 | 263.80 | 288.10 |
| Ar | 78 | 12.45 | 1.991 | 2.81 | 20 | 23.28 | 22.63 | 23.94 |
| Zn | 78 | 28.43 | 1.991 | 6.41 | 3500 | 4336.39 | 4058.47 | 4614.32 |
| Pb | 62 | 23.75 | 2.000 | 6.03 | 400 | 473.22 | 444.67 | 501.77 |

According to the calculation results of the recheck interval and FIGS. 5A-5D, it can be seen that, for Cr in the soil of the site, 36 of the 39 samples were determined as consistent, accounting for 92.31% of the total number of samples, including 6 samples determined to exceed the standard and 30 samples determined not to exceed the standard; the recheck interval of Cr was [263.80, 288.10], and the test values of two samples (5.13%) in this batch fell in this interval, which needed to be verified by ICP test.

For As in the soil of the site, 36 of the 39 samples were determined as consistent, accounting for 92.31% of the total number of samples, including 33 samples determined to exceed the standard and 3 samples determined not to exceed the standard; one point fell in the class I error area, accounting for 2.56% of the total number of samples, its XRF test value was 34.17 mg/kg, while its ICP test value was 19 mg/kg, i.e., the actual determination value did not exceed the standard but the XRF test value exceeded the standard, such that the non-contaminated area was regarded as a contamirecheck interval of Zn was [4058.47, 4614.32], which needed to be verified by ICP test. For Pb in the soil of the site, 30 of the 31 samples were determined as consistent, accounting for 96.77% of the total number of samples, including 3 samples determined to exceed the standard and 27 samples determined not to exceed the standard. The recheck interval of Pb was [444.67, 501.77], and the test value of one sample (3.23%) in this batch fell in this interval, which needed to be verified by ICP test.

Comparing and analyzing the results of the four heavy metal elements, a relatively high proportion (92.31%-97.36%) of data were determined as consistent for site contamination by the XRF and ICP test methods, so XRF test can be used as an effective method to identify and determine site contamination. By observing the data distribution of the four contaminants, it can be seen that the laboratory test values of samples whose XRF test values were far greater or less than the screening values were also far greater or less than the screening values, and for the samples within these concentration ranges, although the test results of the two test methods were different, the determinations based on respective results on the contamination status were consistent. Some studies in the United States have proposed that ICP verification should be carried out for samples below test limits. In fact, according to the analysis here, the test values of samples below the test limits were generally far lower than the screening values, i.e., the determination results of laboratory instrument analysis were consistent with XRF determination results, so it was unnecessary to recheck the samples below the test limits.

However, the points near the screening value of each contaminant were prone to misjudgment, i.e., the recheck interval was near the screening value. Some studies have suggested that the number of samples used for preliminary analysis and verification should not be less than 10% of the total number of samples and generally be near the screening values. According to the analysis here, the proportions of samples in Cr, As, Zn and Pb determination errors were 5.13%, 0, 2.56% and 3.23%, respectively. The proportion of samples in the recheck interval was related to the correlation of the two methods and the concentration distribution of samples used for preliminary analysis. Some cases in the United States used a safety factor of 10% or 20% to determine a recheck interval. According to the analysis here, it can be seen that $C \cdot S/\sqrt{n}$, in Table 2 determines the range of the recheck interval. Because the correlations of different contaminants tested by the two methods were different, $C \cdot S/\sqrt{n}$, was also different. Therefore, it was lack of scientific basis to determine a recheck interval simply by using a safety factor or sample proportion provided artificially.

Comparing the correlation curves of XRF and ICP test values and recheck intervals of heavy metals Cr and As, it can be seen that the recheck intervals were negatively related to the correlations (slope). Generally, the better the correlation was, the smaller the standard deviation between XRF and ICP-inferred XRF' data sets was, the smaller the recheck interval was, and the less the data that needed to be verified by ICP were; on the contrary, the larger the recheck interval was, and the more the data that needed to be verified by ICP were.

With the deepening of site investigation and the understanding of contamination status, the number and proportion of verified samples may decrease, while the number of samples from sites with complex contamination distribution may increase. The combination of XRF technology and ICP verification was helpful to carry out contaminated site investigation. For example, the investigation cost of XRF test combined with limited laboratory verification in a lead contaminated site in the United States were reduced by nearly 50% compared with traditional laboratory analysis alone, and the project cycle was greatly shortened.

This study only analyzed the calculation and application of recheck intervals caused by the uncertainty of XRF test. In addition to the inherent differences in test technology for the uncertainty of XRF, the collection and preparation of samples, the difference in the particle size of soil, the water content, etc., can all affect the results of XRF, and then affect the comparability with ICP. Studies found that the experimental analysis errors were far less than the errors caused by the samples themselves and had little influence on the overall errors. When the XRF test method was used, the fluorescence X-ray energy of different elements was close, which may be interfered by overlapping peaks, such As Pb-Lα and AS-Kα, resulting in overestimation of As test values. Therefore, the test results should be determined before XRF data were used. If the test results exceeded the standard, spectral lines that may cause interference should be selected for analysis and verification.

It can be seen from the above:

①  There was a good correlation between the concentrations of heavy metals tested by the XRF test technology and the traditional laboratory ICP test method, and a relatively high proportion of data were determined as consistent for site contamination by the two methods, so XRF test can be used as an effective method to identify and determine site contamination.

② The interval of possible inconsistency determined by XRF and ICP was generally near the standard value. The analysis showed that it was more reasonable to calculate a recheck interval by the statistical test method, the XRF data in this recheck interval needed to be verified by the ICP test method, and the range of the recheck interval was negatively related to the correlation of data. The recheck intervals of different contaminants in different sites were different, which needed to be calculated from the data of preliminary investigation.

③ This theory and method can also be used in other real-time test technologies. Comparative analysis and mutual verification with laboratory data can be used not only in the stage of site contamination investigation, but also in periodic test and remediation acceptance in the process of restoration. The balance of quantity and accuracy of site test data was beneficial to saving investigation costs and shortening a project cycle.

Finally, it should be noted that the above contents are only used to explain the technical solution of the present invention, but not to limit the protection scope of the present invention. Simple modifications or equivalent substitutions of the technical solution of the present invention by those of ordinary skill in the art do not depart from the essence and scope of the technical solution of the present invention.

What is claimed is:

1. A portable XRF data screening method for heavy metal contaminated soil, comprising the following steps:
   (1) laboratory test: testing a soil sample in a laboratory to obtain a laboratory test value, which is identified as a true value and denoted by LAB;
   (2) XRF test: calibrating an X-ray fluorescence spectrometer with a calibrating sample, and testing pretreated soil with the calibrated X-ray fluorescence spectrometer to obtain an X-ray fluorescence spectrometer test value, which is identified as an estimated value and denoted by XRF; and
   (3) calculation of a recheck interval: dividing test data into four areas by a contaminant screening value $X_c$ as a horizontal line and a correlation-derived site screening value as a vertical line;
   calculating a recheck interval with a number of samples n, a standard value $\mu$ and a sample standard deviation S, specifically comprising:
   ① determining a significant level $\alpha$;
   ② calculating the sample standard deviation S;
   ③ determining a critical value $C=t_\alpha(n-1)$ according to the degree of freedom $df=n-1$ and $\alpha$; and
   ④ calculating a lower recheck interval limit $\mu-C \times S/\sqrt{n}$, and an upper recheck interval limit $\mu+C \times S/\sqrt{n}$, thus obtaining a recheck interval $[\mu-C \times S/\sqrt{n}, \mu+C \times S/\sqrt{n}]$;
   determining, according to the situation that the sample falls into the four areas in the recheck interval, whether or not to further recheck the sample.

2. The method according to claim 1, wherein the significant level in step ① is 0.05 and/or 0.01.

3. The method according to claim 1, wherein the pretreatment in step (2) specifically comprises: air-drying, grinding, sieving and drying the soil sample.

4. The method according to claim 1, wherein the four areas in step (3) are respectively area I, area II, area AA and area BB.

5. The method according to claim 4, wherein the area I is a class I error decision failure area, the area II is a class II error decision failure area, the area AA is an area where both laboratory test and XRF test exceed the standard, and the area BB is an area where both laboratory test and XRF test do not exceed the standard.

6. The method according to claim 4, wherein determining, according to the situation that the sample falls into the four areas in the recheck interval, whether or not to further recheck the sample in step (3) is specifically: when the sample falls into the area I or the area II in the recheck interval, rechecking the sample, otherwise, skipping rechecking the sample.

7. The method according to claim 1, wherein the critical value C in step (3) is obtained from a distribution critical value table.

8. The method according to claim 1, wherein before the recheck interval is calculated in step (3), the method further comprises checking the distribution patterns of XRF and XRF' test data of each contaminant in the site: deriving real-time tested XRF'=(LAB−b)/a according to a correlation formula between the true value and the estimated value: LAB=α×XRF+b; normalizing the values of XRF' and XRF according to a percentage as a pair of parallel samples for statistical test, and if the values obey a normal distribution, performing the next step of calculating a recheck interval, otherwise, if the values do not obey a normal distribution, eliminating relevant test data.

9. Application of the method according to claim 1 in the screening of heavy metal contaminated soil.

* * * * *